US00PP29852P2

(12) United States Plant Patent
Schroll

(10) Patent No.: US PP29,852 P2
(45) Date of Patent: Nov. 20, 2018

(54) ***HYDRANGEA* PLANT NAMED 'SCHROLL121-12-01'**

(50) Latin Name: *Hydrangea macrophylla*
Varietal Denomination: SCHROLL121-12-01

(71) Applicant: Soren Schroll, Odense SV (DK)

(72) Inventor: Soren Schroll, Odense SV (DK)

(73) Assignee: Schroll Management ApS, Odense SV (DK)

( * ) Notice: Subject to any disclaimer, the term of this patent is extended or adjusted under 35 U.S.C. 154(b) by 0 days.

(21) Appl. No.: 15/732,792

(22) Filed: Dec. 28, 2017

(51) Int. Cl.
*A01H 5/02* (2018.01)
*A01H 5/00* (2018.01)

(52) U.S. Cl.
USPC ..... Plt./250
CPC ..... *A01H 5/02* (2013.01); *A01H 5/00* (2013.01)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hydrangea* plant named 'SCHROLL121-12-01', characterized by its compact, upright and mounded plant habit; moderately vigorous growth habit; freely branching habit and strong stems; large mophead-type inflorescences with initially bright green-colored sterile flowers which become bright green and white in color with development; long flowering period; and good postproduction quality and longevity.

2 Drawing Sheets

Botanical designation: *Hydrangea macrophylla.*
Cultivar denomination: 'SCHROLL121-12-01'.

BACKGROUND OF THE INVENTION

The present invention relates to a new and distinct cultivar of *Hydrangea* plant, botanically known as *Hydrangea macrophylla* and hereinafter referred to by the name 'SCHROLL121-12-01'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant originated from a cross-pollination during the spring of 2012 of a proprietary selection of *Hydrangea macrophylla* identified as code number 36-09, not patented, as the female, or seed, parent with a proprietary selection of *Hydrangea macrophylla* identified as code number 66-00, not patented, as the male, or pollen, parent. The new *Hydrangea* plant was discovered and selected by the Inventor in February, 2014 as a flowering plant from within the progeny of the stated cross-pollination in a controlled greenhouse environment in Aarslev, Denmark.

Asexual reproduction of the new cultivar by softwood cuttings in Aarslev, Denmark since the spring of 2014 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL121-12-01'. These characteristics in combination distinguish 'SCHROLL121-12-01' as a new and distinct *Hydrangea* plant:

1. Compact, upright and mounded plant habit.
2. Moderately vigorous growth habit.
3. Freely branching habit and strong stems.
4. Large mophead-type inflorescences with initially bright green-colored sterile flowers which become bright green and white in color with development.
5. Long flowering period.
6. Good postproduction quality and longevity.

Plants of the new *Hydrangea* differ primarily from plants of the female parent selection in the following characteristics:

1. Plants of the new *Hydrangea* are more compact than plants of the female parent selection.
2. Plants of the new *Hydrangea* have smaller and lighter green-colored leaves than plants of the female parent selection.
3. Plants of the new *Hydrangea* and the female parent selection differ in sterile flower color as sterile flowers of plants of the female parent selection are soft pink in color.
4. Plants of the new *Hydrangea* force faster than plants of the female parent selection.

Plants of the new *Hydrangea* differ primarily from plants of the male parent selection in the following characteristics:

1. Plants of the new *Hydrangea* are not as compact as plants of the male parent selection.
2. Plants of the new *Hydrangea* and the male parent selection differ in sterile flower color as sterile flowers of plants of the male parent selection are initially creamy white in color and become green and hot pink in color with development.

3. Plants of the new *Hydrangea* force faster than plants of the male parent selection.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the new *Hydrangea* are more compact than and not as vigorous as plants of 'H213901'.
2. Inflorescences of plants of the new *Hydrangea* have more sterile and fewer fertile flowers than inflorescences of plants of H213901'.
3. Plants of the new *Hydrangea* and 'H213901' differ in sterile flower color as sterile flowers of plants of 'H213901' are dark red purple in color.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the new *Hydrangea* are more compact than and not as vigorous as plants of 'H213906'.
2. Plants of the new *Hydrangea* and 'H213906' differ in sterile flower color as sterile flowers of plants of 'H213906' are dark pink in color.
3. Plants of the new *Hydrangea* force faster than plants of 'H213906'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SCHROLL121-12-01' grown in a container.

The photograph at the top of the second sheet is a close-up view of a typical developing inflorescence of 'SCHROLL121-12-01'.

The photograph at the bottom of the second sheet is a close-up view of a typical developed inflorescence of 'SCHROLL121-12-01'.

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched one time and were one year old when the photographs and description were taken. During the production of the plants, day temperatures ranged from 15° C. to 25° C., night temperatures ranged from 10° C. to 20° C. and light levels ranged from 40 to 50 klux. In the following description, color references are made to The Royal Horticultural Society Colour Chart, 2007 Edition, except where general terms of ordinary dictionary significance are used.

Botanical description: *Hydrangea macrophylla* 'SCHROLL121-12-01'.

Parentage:

*Female, or seed, parent*.—Proprietary selection of *Hydrangea macrophylla* identified as code number 36-09, not patented.

*Male, or pollen, parent*.—Proprietary selection of *Hydrangea macrophylla* identified as code number 66-00, not patented.

Propagation:

*Type cutting*.—By softwood cuttings.

*Time to initiate roots, summer*.—About two weeks at temperatures about 20° C.

*Time to initiate roots, winter*.—About 17 to 18 days at temperatures about 18° C. to 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to N155D, in color.

*Rooting habit*.—Low branching; sparse.

Plant description:

*Plant and growth habit*.—Perennial subshrub; compact, upright and mounded plant habit; broadly inverted triangle; freely branching habit with about six to seven lateral branches developing per plant; strong lateral branches; moderately vigorous growth habit.

*Plant height*.—About 20 cm.

*Plant diameter or area of spread*.—About 35 cm.

*Lateral branches*.—Length: About 20 cm to 25 cm. Diameter: About 5 mm to 6 mm. Internode length: About 3 cm to 4 cm. Strength: Strong. Texture: Smooth, glabrous. Color, developing and developed: Close to 144A. Color, lenticels: Close to N199B.

Leaf description:

*Arrangement*.—Opposite, decussate; simple.

*Length*.—About 10 cm to 12 cm.

*Width*.—About 7 cm.

*Shape*.—Cordate to ovate.

*Apex*.—Cuspidate.

*Base*.—Obtuse to rounded.

*Margin*.—Serrate to dentate.

*Texture and luster, upper surface*.—Rugose, glabrous; semi-glossy to matte.

*Texture and luster, lower surface*.—Rugose, glabrous; prominent venation; matte.

*Venation pattern*.—Pinnate, reticulate.

*Color*.—Developing leaves, upper surface: Close to 137B. Developing leaves, lower surface: Close to 144A. Fully expanded leaves, upper surface: Close to 137A; venation, close to 145A to 145B. Fully expanded leaves, lower surface: Close 137C; venation, close to 145A to 145B.

*Petioles*.—Length: About 2.5 cm to 3 cm. Diameter: About 4 mm. Strength: Strong. Texture, upper and lower surfaces: Smooth, glabrous. Color, upper and lower surfaces: Close to 144B.

Inflorescence & flower description:

*Flower type and habit*.—Showy single sterile and inconspicuous single fertile flowers arranged on terminal mophead-type panicles; panicles hemispherical to flattened globular in overall shape; fertile and sterile flowers face upright to outwardly; early flowering habit, plants begin flowering about eight weeks after forcing period.

*Natural flowering season*.—Long flowering period; continuous flowering from June throughout the summer in Northern Europe.

*Flower longevity, fertile flowers*.—Flowers last about three weeks on the plant; fertile flowers not persistent.

*Flower longevity, sterile flowers*.—Flowers last about four months on the plant; sterile flowers persistent.

*Quantity of flowers*.—Freely flowering habit with less than 20 fertile flowers and about 100 sterile flowers per panicle.

*Fragrance*.—None detected.

*Panicle height*.—About 8 cm.

*Panicle diameter*.—About 13 cm to 14 cm.

*Flower diameter, fertile flowers*.—About 4 mm.

*Flower depth (height), fertile flowers*.—About 3 mm to 4 mm.

*Flower diameter, sterile flowers*.—About 2.5 cm to 3.5 cm.

*Flower depth (height), sterile flowers*.—About 1 cm.

*Flower shape, fertile flowers*.—Spherical.

*Flower shape, sterile flowers*.—Deltoid to reniform.

*Flower buds, fertile flowers*.—Length: About 3 mm. Diameter: About 2 mm. Shape: Spherical. Color: Close to 144A.

*Flower buds, sterile flowers*.—Length: About 3 mm to 5 mm. Diameter: About 3 mm to 4 mm. Shape: Spherical. Color: Close to 144A.

*Petals, fertile flowers*.—Quantity and arrangement: Five in a single whorl. Length: About 4 mm. Width: About 2 mm to 3 mm. Shape: Ovate. Apex: Obtuse. Base: Cuneate. Margin: Entire. Texture, upper and lower surfaces: Smooth, glabrous. Color: When opening and fully opened, upper surface: Close to 77C; towards the margins, close to 142C. When opening and fully opened, lower surface: Close to 77C; towards the margins, close to 142C.

*Petals, sterile flowers*.—Quantity and arrangement: Four in a single whorl. Length: About 5 mm to 6 mm. Width: About 2 mm to 2.5 mm. Shape: Ovate. Apex: Acute. Base: Rounded. Margin: Entire. Texture, upper surface: Fine pubescence. Texture, lower surface: Smooth, glabrous. Color: When opening and fully opened, upper surface: Close to 77B; color does not change with development. When opening and fully opened, lower surface: Close to 77B; color does not change with development.

*Sepals, fertile flowers*.—Quantity and arrangement: Five in a single whorl; imbricate. Length: About 5 mm to 7 mm. Width: About 5 mm. Shape: Ovate. Apex: Acute. Base: Cuneate. Margin: Serrate. Texture, upper and lower surfaces: Smooth, glabrous. Color: When opening and fully opened, upper surface: Close to 144A. When opening and fully opened, lower surface: Close to 146B.

*Sepals, sterile flowers*.—Quantity and arrangement: Three to five in a single whorl; imbricate. Length: About 2 cm to 2.5 cm. Width: About 2 cm to 2.5 cm. Shape: Deltoid to reniform. Apex: Acute to apiculate. Base: Cordate. Margin: Serrate to doubly serrate. Texture, upper surface: Smooth, glabrous. Texture, lower surface: Slightly rippled, glabrous. Color: When opening, upper and lower surfaces: Close to 145A. Fully opened, upper surface: Close to 145A, 144A and 157C; color becoming closer to 143A to 143B with development. Fully opened, lower surface: Close to 144B and 157C; color becoming closer to 144A with development.

*Pedicels, fertile flowers*.—Length: About 8 mm. Diameter: About 1 mm. Strength: Strong. Aspect: Upright to outwardly. Texture: Fine pubescence. Color: Close to 143A to 143B.

*Pedicels, sterile flowers*.—Length: About 1.5 cm. Diameter: About 1.5 mm to 2 mm. Strength: Moderately strong. Aspect: Mostly upright. Texture: Smooth, glabrous. Color: Distally, close to 144C; proximally, close to 70D.

*Reproductive organs, fertile flowers*.—Stamens: Quantity per flower: About eight. Filament length: About 1 mm. Filament color: Close to 143D or 77C. Anther length: About 1.5 mm. Anther shape: Reniform, elongated. Anther color: Close to 77C and 143D. Pollen amount: None observed. Pistils: Pistil quantity per flower: About three. Pistil length: About 1 mm. Stigma shape: Oval. Stigma color: Close to 145D. Style length: About 1.5 mm. Style color: Close to 145D. Ovary color: Close to 145D.

*Reproductive organs, sterile flowers*.—Stamens: Quantity per flower: About eight. Filament length: About 4 mm. Filament color: Close to 77A. Anther length: About 1 mm to 1.2 mm. Anther shape: Rounded, elongated. Anther color: Close to 77C. Pollen amount: Abundant. Pollen color: Close to 18B. Pistils: Pistil quantity per flower: About three. Pistil length: About 1 mm. Stigma shape: Roughly oval. Stigma color: Close to 77A. Style length: About 1 mm. Style color: Close to 77A. Ovary color: Close to 77A.

*Seeds*.—Quantity: Few to none. Length: About 0.5 mm. Diameter: About 0.1 mm. Color: Close to 164C.

Pathogen & pest resistance: Plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 4° C. to 35° C.

It is claimed:

1. A new and distinct *Hydrangea* plant named 'SCHROLL121-12-01' as illustrated and described.

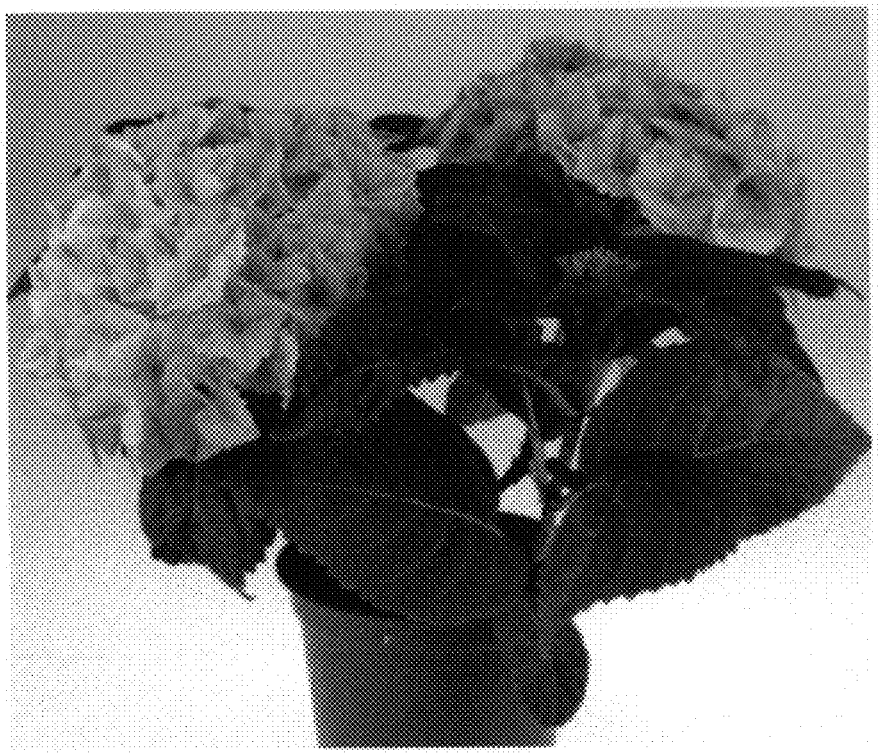

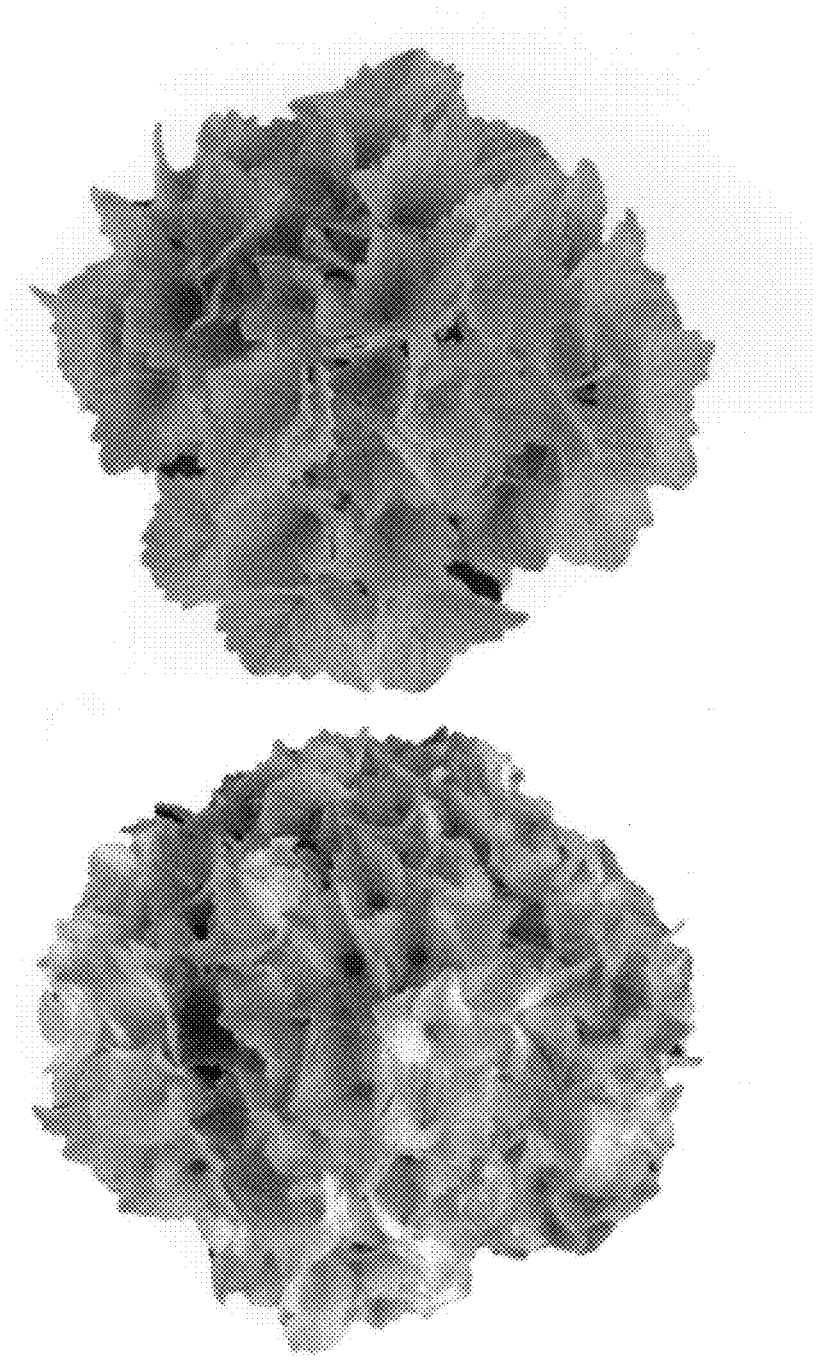

* * * * *